United States Patent
Ken

(10) Patent No.: US 6,293,960 B1
(45) Date of Patent: *Sep. 25, 2001

(54) CATHETER WITH SHAPE MEMORY POLYMER DISTAL TIP FOR DEPLOYMENT OF THERAPEUTIC DEVICES

(75) Inventor: Christopher G. M. Ken, San Mateo, CA (US)

(73) Assignee: Micrus Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,297

(22) Filed: May 22, 1998

(51) Int. Cl.[7] ................................................. A61M 29/00

(52) U.S. Cl. ............................................................ 606/195

(58) Field of Search .................................... 606/195, 194, 606/196, 197, 198, 191; 604/103, 91; 128/898

(56) References Cited

U.S. PATENT DOCUMENTS

| Re. 32,348 | 2/1987 | Pevsner . |
|---|---|---|
| 1,341,052 | 5/1920 | Gale . |
| 1,667,730 | 5/1928 | Green . |

(List continued on next page.)

FOREIGN PATENT DOCUMENTS

| 4102550 A1 | 8/1991 | (DE) . |
|---|---|---|
| 0 183372 A1 | 6/1986 | (EP) . |
| 0 358 767 A1 | 3/1990 | (EP) . |
| 0 382014 A1 | 8/1990 | (EP) . |
| 592.182 | 7/1925 | (FR) . |
| 2 066 839 A | 7/1981 | (GB) . |
| WO 97/48351 | 12/1997 | (WO) . |

OTHER PUBLICATIONS

Retrievable Gianturco–Coil Introducer, By Jeffrey Hawkins, Ronald G. Quisling, MD, J. Parker Mickle, MD an Irvin F. Hawkins, MD (Radiology 1986) From the Depts. Of Radiology and Neurosurgery, University of Florida Medical Center and Hawk Prototype Equipment, Gainesville, FL.

Christos A. Athanasoulis, M.D. The New England Journal of Medicine, May 15, 1980 "Therapeutic Application of Angiography" pp. 1117–1125 (1 of 2).

Christos A. Athanasoulis, M.D. The New England Journal of Medicine, May 22, 1980 "Therapeutic Applications of Angiography" pp. 1174–1179 (2 of 2).

Alex Berenstein, M.D. and Irwin I. Kricheff, M.D. "Catheter and Material Selection for Transarterial Embolization: Technical Considerations" Radiology, Sep. 1979; pp. 631–639.

(List continued on next page.)

Primary Examiner—Henry J. Recla
Assistant Examiner—(Jackie)Tan-Uyen T. Ho
(74) Attorney, Agent, or Firm—Fulwider Patton Lee & Utecht, LLP

(57) ABSTRACT

The occlusion balloon catheter includes an elongated tubular catheter body having a fluid lumen for inflation of an occlusion balloon detachably mounted to the catheter body by a tubular shape memory collar. The occlusion balloon includes a valve for sealing the occlusion balloon when it is inflated, and the collar of shape memory material clamps onto a stem of the valve. The shape memory collar can be heated by a fiber optic pusher member threaded through the catheter body to cause the collar to assume an enlarged configuration disconnecting the occlusion balloon. A method of detaching the occlusion balloon from the occlusion balloon catheter involves the steps of placing the occlusion balloon catheter within a guiding catheter, and placing the guiding catheter within the vasculature so that the distal opening of the guiding catheter extends into an aneurysm or other deformation to be treated. The fiber optic pusher is then used to expel the device into the aneurysm.

12 Claims, 2 Drawing Sheets

U.S. PATENT DOCUMENTS

| | | |
|---|---|---|
| 2,078,182 | 4/1937 | MacFarland . |
| 2,549,335 | 4/1951 | Rahthus . |
| 3,334,629 | 8/1967 | Cohn . |
| 3,417,746 | 12/1968 | Moore et al. . |
| 3,649,224 | 3/1972 | Anderson et al. . |
| 3,868,956 | 3/1975 | Alfidi et al. . |
| 4,327,734 | 5/1982 | White, Jr. . |
| 4,341,218 * | 7/1982 | U .......................................... 128/325 |
| 4,402,313 * | 9/1983 | Handa et al. ........................ 606/195 |
| 4,402,319 | 9/1983 | Handa et al. . |
| 4,441,495 | 4/1984 | Hicswa . |
| 4,494,531 | 1/1985 | Gianturco . |
| 4,512,338 | 4/1985 | Balko et al. . |
| 4,545,367 * | 10/1985 | Tucci .................................... 128/898 |
| 4,638,803 | 1/1987 | Rand . |
| 4,655,771 | 4/1987 | Wallsten . |
| 4,718,907 | 1/1988 | Karwoski et al. . |
| 4,732,152 | 3/1988 | Wallsten et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,913,701 * | 4/1990 | Tower .................................. 604/103 |
| 4,934,743 * | 6/1990 | Kapgan et al. ........................ 285/23 |
| 4,944,746 | 7/1990 | Iwata et al. . |
| 4,954,126 | 9/1990 | Wallsten . |
| 4,957,479 | 9/1990 | Roemer . |
| 4,957,501 | 9/1990 | Lahille et al. . |
| 4,969,709 | 11/1990 | Sogawa et al. . |
| 4,969,890 | 11/1990 | Sugita et al. . |
| 4,990,155 | 2/1991 | Wilkoff . |
| 4,994,069 | 2/1991 | Ritchart et al. . |
| 5,002,556 * | 3/1991 | Ishida et al. ........................ 606/191 |
| 5,026,377 | 6/1991 | Burton et al. . |
| 5,041,084 | 8/1991 | DeVries et al. . |
| 5,058,936 * | 10/1991 | Kapgan et al. ...................... 285/382 |
| 5,064,435 | 11/1991 | Porter . |
| 5,071,407 | 12/1991 | Termin et al. . |
| 5,104,404 | 4/1992 | Wolff . |
| 5,108,407 * | 4/1992 | Geremia et al. ...................... 606/108 |
| 5,122,136 | 6/1992 | Guglielmi et al. . |
| 5,133,731 | 7/1992 | Butler et al. . |
| 5,133,732 | 7/1992 | Wiktor . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,176,625 | 1/1993 | Brisson . |
| 5,176,661 | 1/1993 | Evard et al. . |
| 5,181,921 | 1/1993 | Makita et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,222,969 | 6/1993 | Gillis . |
| 5,222,970 | 6/1993 | Reeves . |
| 5,226,911 | 7/1993 | Chee et al. . |
| 5,228,453 | 7/1993 | Sepetka . |
| 5,234,456 | 8/1993 | Silvestrini . |
| 5,250,071 | 10/1993 | Palermo . |
| 5,304,194 | 4/1994 | Chee et al. . |
| 5,312,152 | 5/1994 | Woebkenberg, Jr. et al. . |
| 5,312,415 | 5/1994 | Palermo . |
| 5,336,205 | 8/1994 | Zenzen et al. . |
| 5,341,818 | 8/1994 | Abrams et al. . |
| 5,342,387 | 8/1994 | Summers . |
| 5,350,397 | 9/1994 | Palermo et al. . |
| 5,354,295 | 10/1994 | Guglielmi et al. . |
| 5,366,442 | 11/1994 | Wang et al. . |
| 5,368,049 | 11/1994 | Raman et al. . |
| 5,378,236 | 1/1995 | Seifert . |
| 5,382,259 | 1/1995 | Phelps et al. . |
| 5,411,475 | 5/1995 | Atala et al. . |
| 5,423,829 | 6/1995 | Pham et al. . |
| 5,441,516 | 8/1995 | Wang et al. . |
| 5,443,478 | 8/1995 | Purdy . |
| 5,514,176 | 5/1996 | Bosley, Jr. . |
| 5,522,836 | 6/1996 | Palermo . |
| 5,531,716 | 7/1996 | Luzio et al. . |
| 5,540,680 | 7/1996 | Guglielmi et al. . |
| 5,549,624 | 8/1996 | Mirigian et al. . |
| 5,562,641 | 10/1996 | Flomenblit et al. . |
| 5,562,698 | 10/1996 | Parker . |
| 5,569,245 | 10/1996 | Guglielmi et al. . |
| 5,578,074 | 11/1996 | Mirigian . |
| 5,582,619 | 12/1996 | Ken . |
| 5,607,445 | 3/1997 | Summers . |
| 5,624,461 | 4/1997 | Mariant . |
| 5,637,086 | 6/1997 | Ferguson et al. . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,558 | 7/1997 | Horton . |
| 5,649,949 | 7/1997 | Wallace et al. . |
| 5,662,712 * | 9/1997 | Pathak et al. ........................ 606/195 |
| 5,667,522 | 9/1997 | Flomenblit et al. . |
| 5,669,905 | 9/1997 | Sheldrup et al. . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,695,111 | 12/1997 | Nanis et al. . |
| 5,741,323 | 4/1998 | Pathak et al. . |
| 5,746,769 | 5/1998 | Ton et al. . |
| 5,749,894 | 5/1998 | Engelson . |
| 5,779,281 * | 7/1998 | Kapgan et al. ................. 285/148.19 |
| 5,797,920 | 8/1998 | Kim . |
| 5,814,062 | 9/1998 | Sepetka et al. . |
| 5,944,733 | 8/1999 | Engelson . |
| 5,989,242 * | 11/1999 | Saadat et al. ........................... 606/1 |

OTHER PUBLICATIONS

O.A. Battista, Et Al. Journal of Applied Polymer Science 1967 "Colloidal Macromolecular Phenomena. Part II. Novel Microcrystals of Polymers" pp. 481–498.

Sadek K. Hilal, M.D. Et Al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. Et Al. Investigative Radiology, May–Jun. 1978 "Transcatheter Embolization with Microfibrillar Collagen in Swine"; pp. 200–204.

Ashok J. Kumar, Et Al., Journal of Neuroradiology (1982) "Preoperative Embolization of Hypervascular Head and Neck Neoplasms Using Microfibrillar Collagen", pp. 163–168.

Richard E. Latchaw, M.D. Et Al., Radiology (1979) "Polyvinyl Foam Embolization of Vascular and Neoplastic Lesions of the Head, Neck and Spine" pp. 669–679.

Stewart R. Reuter, M.D. Et Al. American Journal of Radiology, Sep. 1975 "Selective Arterial Embolization for Control of Massive Upper Gastrointestinal Bleeding" pp. 119–126.

Glenn H. Roberson Et Al., American Journal of Radiology, Oct 1979 "Therapeutic Embolization of Juvenile Angiofibroma" pp. 657–663.

Sidney Wallace, M.D. Et Al., Cancer, Oct. 1979 "Arterial Occlusion of Pelvic Bone Tumors"; pp. 322–325 & 661–663.

"Mechanical Devices for Arterial Occlusion" By C. Gianturco, M.D., Et Al., Jul. 1975 pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", by James H. Anderson, et al., Am. J. Roentgenol, Nov. 1977, pp. 795–798.

"'Mini' Gianturco Stainless Steel Coils for Transcatheter Vascular Occlusion" By James H. Anderson, Et Al., from the Department of Diagnostic Radiology at the University of Texas System Cancer Center , Aug. 1978, pp. 301–303.

"A New Improved Coil for Tapered–Tip Catheter for Arterial Occlusion" by Vincent P. Chuang, M.D., Et Al., May 1980, pp. 507–509.

Copy of the International Search Report Relating to PCT/US99/07953 Dated Aug. 24, 1999.

* cited by examiner

CATHETER WITH SHAPE MEMORY POLYMER DISTAL TIP FOR DEPLOYMENT OF THERAPEUTIC DEVICES

BACKGROUND OF THE INVENTION

1. Field of the Invention

This invention relates generally to devices for interventional therapeutic treatment or vascular surgery for treatment of defects in the vasculature, and more particularly concerns a system and method for detaching occlusion balloons for treatment of aneurysms.

2. Description of Related Art

Vasoocclusive devices are typically placed within the vasculature of the human body by use of a catheter, either to block the flow of blood through a vessel making up that portion of the vasculature through the formation of an embolus or to form such an embolus within an aneurysm stemming from the vessel. Vasoocclusive devices used for these procedures can have a variety of configurations, and are generally formed of one or more elements that are larger in the deployed configuration than when they are within the delivery catheter prior to placement. One anatomically shaped vasoocclusive device that forms itself into a shape of an anatomical cavity such as an aneurysm is made of a preformed strand of flexible material such as a nickel-titanium alloy. One or more of such vasoocclusive members can be wound to form a generally spherical or ovoid shape in a relaxed, expanded state.

Aneurysms have been treated with external surgically placed clips, or using vascular catheters, by detachable vasoocclusive balloons or an embolus generating vasoocclusive device such as one or more vasoocclusive coils. The delivery of such vasoocclusive devices can be accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area of interest, such as an aneurysm.

Some conventional vasoocclusive devices are operated by pulling or jerking the catheter tip from the balloon, thus potentially compromising the position of the implant. One such device provides for an endovascular wire and tip that can be separated from the holding wire mechanically or electrolytically for the formation of thrombus in blood vessels. However, such devices that release the interventional device by mechanically breaking an intermediate section between the catheter tip and balloon can potentially leave broken or jagged ends that can potentially injure the vasculature.

One conventional releasable balloon catheter used to embolize vascular lesions has a tube portion made of a material such as a hydrophilic polymer, located between the catheter and the balloon, that can be broken by torsion of the tube. The tube can be melted by heating the tube, or can be dissolved in the blood when heated, and electrodes are provided for heating the tube. Another conventional technique for separating a balloon from a balloon catheter involves the melting and breaking of a connecting member made from polyvinyl alcohol or trans-polyisoprene between the balloon and the catheter body, when power is supplied to electrodes provided for heating the connecting member. When the connecting member is heated to temperatures of about 70° C. and slight tension is applied, the balloon can be separated from the main catheter body. However, such devices that release the interventional device by melting or dissolving the intermediate section between the catheter tip and balloon can also potentially release undesirable particles of materials into the bloodstream.

There is therefore a need for a precise method of detaching occlusion balloons or other therapeutic interventional devices without compromising the position of the implant, without presenting broken or jagged ends that can potentially injure the vasculature, and without releasing undesirable particles of materials into the bloodstream. It is therefore desirable to provide a method and system for cleanly releasing occlusion balloons from a placement catheter for treatment of aneurysms. The present invention meets these needs.

SUMMARY OF THE INVENTION

Briefly, and in general terms, the present invention provides for an occlusion balloon catheter and a precise system and method of for cleanly releasing an implant such as an occlusion balloon or other occlusion device from the occlusion balloon catheter for use in interventional therapy and vascular surgery, and which is adapted to be inserted into a portion of a vasculature for treatment of a body vessel such as an aneurysm without compromising the position of the implant.

In a presently preferred aspect of the invention, the occlusion balloon catheter comprises an elongated tubular catheter body or shaft having a fluid lumen in fluid communication with a detachable occlusion balloon for inflation of the occlusion balloon. Mounting means are also provided for detachably mounting an occlusion balloon to a tubular catheter body and for detaching the occlusion balloon for deployment when a desired placement within an aneurysm to be treated and out of a parent vessel is achieved. The mounting means preferably comprises a collar of shape memory material disposed on the distal tip of the tubular catheter body and connecting the occlusion balloon to the tubular catheter body. In one presently preferred embodiment, the occlusion balloon comprises a valve permitting the inflation of the occlusion balloon through the inflation lumen of the occlusion balloon catheter, and sealing the occlusion balloon once the occlusion balloon is inflated, and the collar of shape memory material clamps onto the valve of the occlusion balloon. In one aspect, the external surface of the valve is grooved to improve gripping of the shape memory collar onto the occlusion balloon valve. The shape memory collar can be heated to thereby assume a configuration disconnecting the occlusion balloon and the placement catheter body. In a currently preferred embodiment, a fiber optic can be threaded through the catheter shaft and connected to an optical light source for conducting light energy to the collar to heat the collar and to thereby induce the collar to assume an enlarged configuration to detach the occlusion balloon from the placement collar.

In a presently preferred embodiment of the method of using the invention, the occlusion balloon catheter is placed within a guiding catheter. The guiding catheter is then placed within the vasculature so that the distal opening of the guiding catheter extends into an aneurysm or other deformation to be treated. A fiber optic pusher is then used to expel the device into the aneurysm. In a presently preferred aspect of the invention, the fiber optic is threaded through the occlusion balloon catheter after the balloon is inflated and ready for detachment and up to the shape memory collar that can be heated by the energy transmitted through the optical fiber to cause the shape memory material to assume a shape that releases the balloon from the occlusion balloon catheter. In other presently preferred embodiments, the balloon can be released by other means, such as thermomechanical, electromagnetic or electro-dissolution of the coupling between the device and the pusher.

The method of the invention for closing and occluding an opening of an aneurysm from a parent blood vessel accordingly thus comprises the steps of attaching an occlusion balloon to the distal end of a occlusion balloon catheter, enclosing the occlusion balloon catheter and occlusion balloon in a lumen of a guiding catheter, with the occlusion balloon catheter proximal of the occlusion balloon, positioning the guiding catheter so that the distal opening of the guiding catheter is in the opening between the aneurysm and the parent blood vessel, pushing the occlusion balloon into the aneurysm by extending the occlusion balloon catheter towards the distal end of the guiding catheter, inflating the occlusion balloon with inflation fluid conducted through the occlusion balloon catheter, and disconnecting the occlusion balloon from the occlusion balloon catheter, thereby deploying the occlusion balloon within the aneurysm and at least partially occluding the opening between the aneurysm and the parent blood vessel. In a presently preferred aspect of the method, the step of disconnecting the occlusive apparatus from the occlusion balloon catheter comprises causing energy to be transmitted through a fiber optic threaded through the occlusion balloon catheter to release the connection between the occlusion balloon catheter and the occlusion balloon.

These and other aspects and advantages of the invention will become apparent from the following detailed description and the accompanying drawings, which illustrate by way of example the features of the invention.

DETAILED DESCRIPTION OF THE PREFERRED EMBODIMENTS

Vasoocclusive devices that are operated by pulling or jerking the catheter tip from the balloon can compromise the position of the implant, while other devices that release such devices by breaking an intermediate section between the catheter tip and balloon can potentially injure the vasculature, and those that melt or dissolve an intermediate section can release undesirable particles of materials into the bloodstream.

Figure 1:
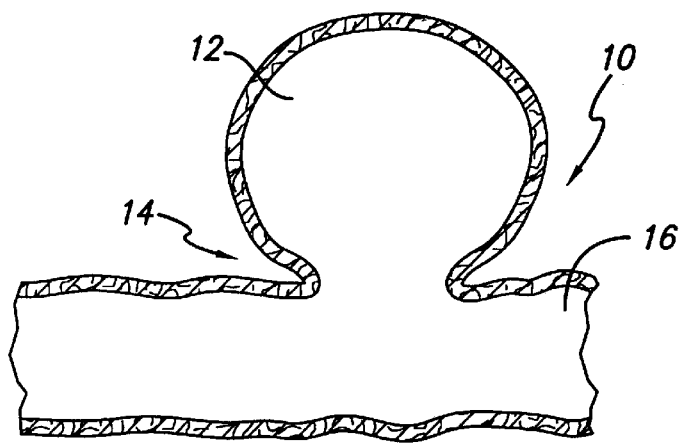
FIG. 1 is an illustration of an aneurysm.

As is illustrated in the drawings, which are provided for the purposes of illustration and not by way of limitation, the invention is accordingly embodied in a system and method for detaching an occlusion balloon from a balloon catheter shaft for treatment of aneurysms, such as the aneurysm 10 illustrated in FIG. 1 and having a dome portion 12, a neck portion 14, and a parent vessel 16. In one presently preferred embodiment, the occlusion balloon catheter includes a shape memory polymer collar at the distal tip of the catheter and releasably attached to an occlusion balloon.

Figure 2:
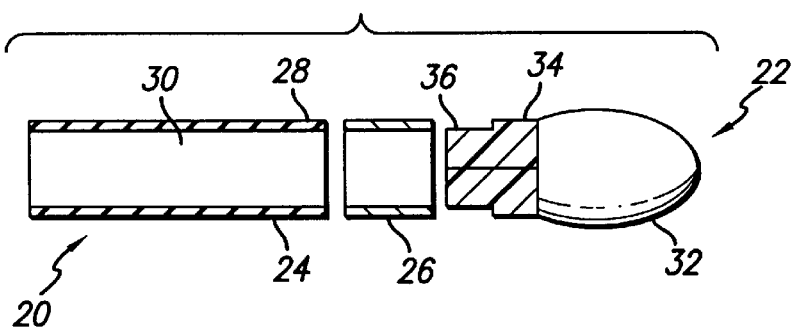
FIG. 2 is an exploded side sectional view of a distal end portion of an occlusion balloon catheter having a shape memory distal tip according to the present invention, showing the shape memory collar in a first, open configuration.
Figure 3:
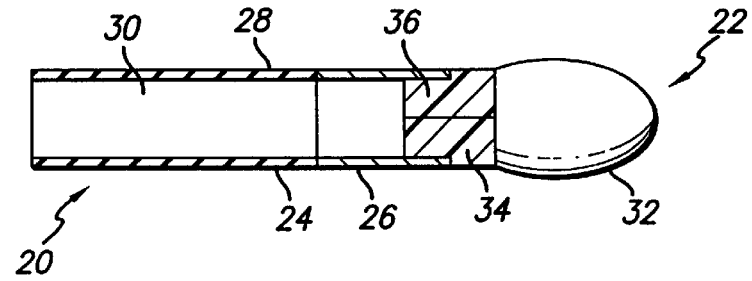
FIG. 3 is a side sectional view of the occlusion balloon catheter of FIG. 2, showing the shape memory collar in a second, closed or narrowed configuration.

With reference to FIG. 2, the occlusion balloon catheter 20 comprises an elongated tubular catheter body or shaft 24 connected to an occlusion balloon 22 by a mounting means 26 that is preferably a tubular, shape memory collar having a closed or narrowed configuration (illustrated in FIG. 3) with a relatively smaller inner diameter, in which the occlusion balloon is connected to the catheter body, and an open configuration (illustrated in FIG. 2) with a relatively larger inner diameter, in which the occlusion balloon can be detached when the balloon is placed in position and inflated. The occlusion balloon can, for example, be formed from polymeric materials that have been commonly been used for making balloon catheters, such as polyethylene, polyolefins, polyvinyl chloride, polyester, polyamide, polyethylene terephthalate (PET), polyamides, nylon, polyurethane, and the like.

The catheter body has a fluid lumen 30, and is connected to a proximal hub (not shown) providing a source of pressurized inflation fluid for inflating the balloon. The occlusion balloon has an inflatable balloon portion 32 and a self-sealing valve 34 permitting the inflation of the occlusion balloon through the inflation lumen of the occlusion balloon catheter, and sealing the occlusion balloon once the occlusion balloon is inflated. The valve is typically attached to the balloon portion by adhesive.

Figure 4:
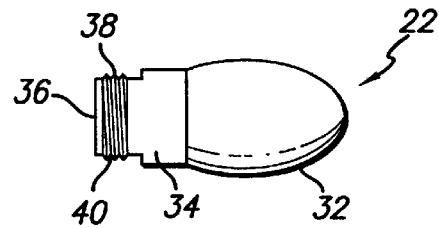
FIG. 4 is a side sectional view of an alternate embodiment of an occlusion balloon of the occlusion balloon catheter of FIG. 2, having ridges on the surface of the valve stem of the occlusion balloon.

The shape memory collar is preferably attached to the distal end 28 of the catheter body by an adhesive that retains high strength at temperatures beyond the shape memory material transition point. The shape memory collar is preferably heat treated in a opened releasing configuration illustrated in FIG. 2, and can be heated to a temperature that allows the collar to be worked and crimped into a narrowed gripping configuration shown in FIG. 3 gripping over an elongated stem portion 36 of the valve of the occlusion balloon to connect the occlusion balloon to the catheter body. In another preferred aspect, illustrated in FIG. 4, the stem portion of the valve can have a surface defining a plurality of ridges 38 and grooves 40 to aid in the connection of the collar to the stem of the valve.

Figure 5:
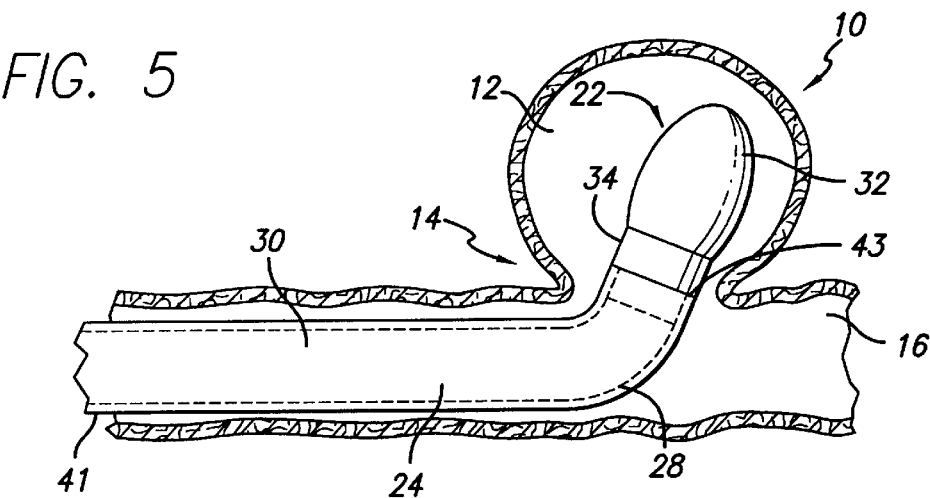
FIG. 5 is an illustration of an occlusion balloon in a deflated condition on an occlusion balloon catheter shaft according to the invention, being inserted within an aneurysm.

As is illustrated in FIG. 5, the occlusion balloon catheter is placed within a guiding catheter 41. The guiding catheter is then placed within the vasculature so that the distal opening 43 of the guiding catheter extends into the aneurysm or other deformation to be treated. When the occlusion balloon of the balloon catheter has been placed within the dome of the aneurysm as illustrated in FIG. 5, and when an operator is satisfied that the device is properly deployed, the balloon is inflated through the catheter. The shape memory collar can then be heated to be induced to shrink and pull back to assume the enlarged configuration shown in FIG. 2, disconnecting the valve of the balloon from the catheter shaft.

Figure 6:
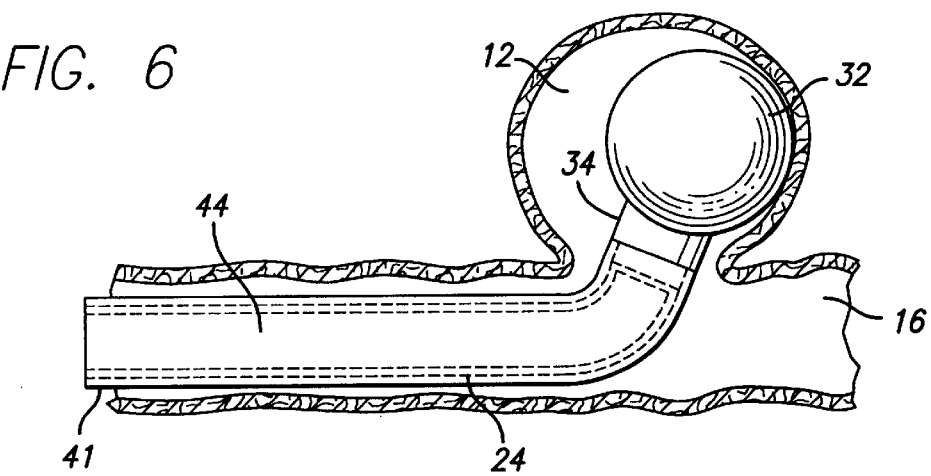
FIG. 6 is an illustration of the occlusion balloon of FIG. 5 inserted within an aneurysm, in an inflated condition.
Figure 7:
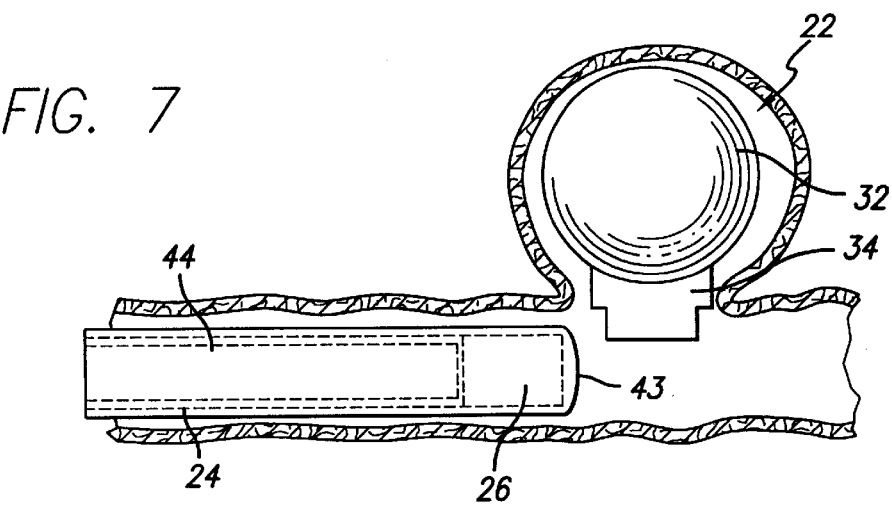
FIG. 7 is an illustration of the inflated occlusion balloon of FIG. 6 being detached and deployed within an aneurysm.

Referring to FIG. 6, a fiber optic pusher 44 can be inserted through the lumen of the occlusion balloon catheter body and advanced to the location of a shape memory polymer valve juncture, where it can then be used to expel the device into the aneurysm. The fiber optic is thus preferably threaded through the occlusion balloon catheter body up to the shape memory collar that can be heated by the energy transmitted through the optical fiber to cause the shape memory material to assume a shape that releases the balloon from the occlusion balloon catheter. Thereafter, the fiber optic can then be advanced further to push the occlusion balloon free of the catheter. The proximal end (not shown) of the fiber optic pusher member is preferably connected to an optical light source (not shown) for conducting coherent light energy transmitted at the distal end of the fiber optic pusher member to the shape memory collar, in order to heat the shape memory collar and cause it to return to its previous more open shape to induce the collar to detach the valve of the occlusion balloon from the catheter shaft. The balloon can also be released by other suitable means, such as by thermomechanical, electromagnetic or electro-dissolution of the coupling between the device and the pusher. As is illustrated in FIG. 7, the occlusion balloon valve is then released from the occlusion balloon catheter tip, and the guiding catheter and occlusion balloon catheter are then withdrawn, leaving the inflated occlusion balloon remaining in place within the aneurysm.

In a presently preferred embodiment, the shape memory collar is formed from a shape memory material such as nickel titanium alloy, that can be heat treated to have shape memory behavior, such that the alloy has a desired closed configuration at a temperature appropriate for introduction into the body via a catheter, and after placement, the collar will take on a more open shape for detaching the valve of the occlusion balloon from the catheter shaft.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter for release and deployment of a therapeutic device within the vasculature of a patient, comprising:

an elongated tubular catheter body having a distal tip;

a therapeutic device comprising an occlusion balloon; and a collar of shape memory material disposed on the distal tip of the catheter body and connecting the therapeutic device to the catheter body for placement of the therapeutic device within the vasculature, said collar having a narrowed configuration and an enlarged configuration, said collar having an inner diameter that is smaller in said narrowed configuration than in said enlarged configuration, said collar in said narrowed configuration connecting the therapeutic device to the catheter body, and said collar in said enlarged configuration detaching the therapeutic device from the catheter body for deploying the therapeutic device when a desired placement of the therapeutic device within the vasculature is achieved, and wherein said shape memory collar can be heated to thereby assume said enlarged configuration disconnecting the therapeutic device and the catheter body.

2. The catheter of claim 1, wherein said therapeutic device comprises a stem, and said collar is crimped over said stem.

3. The catheter of claim 2, wherein said stem has an external surface that is grooved to improve gripping of the shape memory collar onto the stem.

4. The catheter of claim 1, wherein said tubular catheter body includes a fluid lumen, and wherein said occlusion balloon comprises an inflatable balloon portion in fluid communication with the fluid lumen of the tubular catheter body for inflation of the occlusion balloon, and a valve connecting the fluid lumen of the catheter body with the inflatable balloon portion of the occlusion balloon, permitting inflation of the occlusion balloon through the inflation lumen of the occlusion balloon catheter, and said valve sealing the occlusion balloon once the occlusion balloon is inflated.

5. The catheter of claim 1, wherein said shape memory collar is made of nickel titanium alloy.

6. A catheter for release and deployment of a therapeutic device within the vasculature of a patient, comprising:

an elongated tubular catheter body having a distal tip;

a therapeutic device comprising an occlusion balloon;

a collar of shape memory material disposed on the distal tip of the catheter body and connecting the therapeutic device to the catheter body for placement of the therapeutic device within the vasculature, said collar having a narrowed configuration and an enlarged configuration, said collar having an inner diameter that is smaller in said narrowed configuration than in said enlarged configuration, said collar in said narrowed configuration connecting the therapeutic device to the catheter body, and said collar in said enlarged configuration detaching the therapeutic device from the catheter body for deploying the therapeutic device when a desired placement of the therapeutic device within the vasculature is achieved; and a fiber optic member adapted to be threaded through the catheter body to the collar and connected to an optical light source for conducting light energy to the collar to heat the collar and to thereby induce the collar to assume said enlarged configuration to detach the therapeutic device from the collar.

7. An occlusion balloon catheter for treatment of a malformation in a body vessel, the vessel having an enlarged portion and a narrow opening into another vessel, the occlusion balloon catheter comprising:

an elongated tubular catheter body having a fluid lumen and a distal tip;

an occlusion balloon detachably mounted to said elongated tubular catheter body, said occlusion balloon having an inflatable balloon portion in fluid communication with the fluid lumen of the tubular catheter body for inflation of the occlusion balloon and a valve permitting the inflation of the occlusion balloon through the fluid lumen of the occlusion balloon catheter, and sealing the occlusion balloon once the occlusion balloon is inflated; and a collar of shape memory material disposed on the distal tip of the tubular catheter body and connecting the occlusion balloon to the tubular catheter body for detachably mounting the occlusion balloon to the occlusion balloon catheter body and for detaching the occlusion balloon for deployment when a desired placement of the occlusion balloon is achieved, said collar having a narrowed configuration and an enlarged configuration, said collar having an inner diameter that is smaller in said narrowed configuration than in said enlarged configuration, said collar in said narrowed configuration connecting the therapeutic device to the catheter body, and said collar in said enlarged configuration detaching and deploying the therapeutic device, and wherein said shape memory collar can be heated to thereby assume said enlarged configuration disconnecting the occlusion balloon and the catheter body.

8. The occlusion balloon catheter of claim 7, wherein said collar is crimped over said valve.

9. The occlusion balloon catheter of claim 8, wherein said valve has a stem, said collar is crimped over said stem, and said stem has an external surface that is grooved to improve gripping of the shape memory collar onto the valve.

10. The occlusion balloon catheter of claim 7, wherein said shape memory collar is made of nickel titanium alloy.

11. An occlusion balloon catheter for treatment of a malformation in a body vessel, the vessel having an enlarged portion and a narrow opening into another vessel the occlusion balloon catheter comprising:

an elongated tubular catheter body having a fluid lumen and a distal tip;

an occlusion balloon detachably mounted to said elongated tubular catheter body, said occlusion balloon having an inflatable balloon portion in fluid communication with the fluid lumen of the tubular catheter body for inflation of the occlusion balloon and a valve permitting the inflation of the occlusion balloon through the fluid lumen of the occlusion balloon catheter, and sealing the occlusion balloon once the occlusion balloon is inflated;

a collar of shape memory material disposed on the distal tip of the tubular catheter body and connecting the occlusion balloon to the tubular catheter body for detachably mounting the occlusion balloon to the occlusion balloon catheter body and for detaching the occlusion balloon for deployment when a desired placement of the occlusion balloon is achieved said collar having a narrowed configuration and an enlarged configuration, said collar having an inner diameter that is smaller in said narrowed configuration than in said enlarged configuration, said collar in said narrowed configuration connecting the therapeutic device to the catheter body, and said collar in said enlarged configuration detaching and deploying the therapeutic device; and a fiber optic member adapted to be threaded through the catheter body to the collar and connected to an optical light source for conducting light energy to the collar to heat the collar and to thereby induce the collar to assume said enlarged configuration to detach the therapeutic device from the collar.

12. A method for closing and occluding an opening of an aneurysm, the aneurysm having a dome portion and a neck opening into a parent vessel of a patient's vasculature, the steps of the method comprising:

attaching an occlusion balloon to the distal end of a occlusion balloon catheter by a shape memory collar;

enclosing the occlusion balloon catheter and occlusion balloon in a lumen of a guiding catheter, with the occlusion balloon catheter proximal of the occlusion balloon;

positioning the guiding catheter within a patient's vasculature so that the distal opening of the guiding catheter extends into an aneurysm;

pushing the occlusion balloon through the guiding catheter into the aneurysm by extending the occlusion balloon catheter toward the distal end of the guiding catheter;

inflating the occlusion balloon with inflation fluid conducted through the occlusion balloon catheter; and threading a fiber optic member through the occlusion balloon catheter to expel the occlusion balloon into the aneurysm, and causing energy to be transmitted through the fiber optic member threaded through the occlusion balloon catheter to the shape memory collar to heat the shape memory collar to cause the shape memory collar to expand to release the occlusion balloon, thereby deploying the occlusion balloon within the aneurysm and at least partially occluding the opening between the aneurysm and the parent blood vessel.

* * * * *